(12) United States Patent
Zhang et al.

(10) Patent No.: US 8,389,028 B2
(45) Date of Patent: Mar. 5, 2013

(54) METHOD FOR PROMOTING EYE HEALTH

(75) Inventors: Jin Zhang, Clayton, OH (US); Michael Griffin Hayek, Dayton, OH (US)

(73) Assignee: The Iams Company, Cincinnati, OH (US)

( * ) Notice: Subject to any disclaimer, the term of this patent is extended or adjusted under 35 U.S.C. 154(b) by 0 days.

(21) Appl. No.: 13/188,579

(22) Filed: Jul. 22, 2011

(65) Prior Publication Data

US 2011/0274782 A1    Nov. 10, 2011

(51) Int. Cl.
*A01N 65/00*    (2009.01)

(52) U.S. Cl. ........................................... 424/725

(58) Field of Classification Search ................. None
See application file for complete search history.

(56) References Cited

U.S. PATENT DOCUMENTS

| | | | |
|---|---|---|---|
| 6,080,788 A | 6/2000 | Sole et al. |
| 6,156,355 A | 12/2000 | Shields et al. |
| 6,200,601 B1 | 3/2001 | Gorenbein et al. |
| 6,254,898 B1 | 7/2001 | Bragaglia |
| 6,313,165 B1 | 11/2001 | Grunberger et al. |
| 6,329,432 B2 | 12/2001 | Howard et al. |
| 6,646,013 B1 | 11/2003 | Barker et al. |
| 6,649,195 B1 | 11/2003 | Gorsek |
| 6,974,841 B1 | 12/2005 | Rapisarda |
| 8,012,513 B2 | 9/2011 | Zhang et al. |
| 2001/0043983 A1 | 11/2001 | Hamilton |
| 2002/0076469 A1 | 6/2002 | Zicker et al. |
| 2004/0220118 A1 | 11/2004 | Bland et al. |
| 2004/0248763 A1 | 12/2004 | Freeman et al. |
| 2005/0074447 A1 | 4/2005 | Papas et al. |
| 2005/0112210 A1 | 5/2005 | Grossman et al. |
| 2005/0136130 A1 | 6/2005 | Lang |
| 2005/0266051 A1 | 12/2005 | Kelley et al. |
| 2006/0134014 A1 | 6/2006 | Scherl et al. |
| 2006/0251750 A1 | 11/2006 | Tabor |
| 2007/0286925 A1 | 12/2007 | Zhang et al. |
| 2011/0274782 A1 | 11/2011 | Zhang et al. |

FOREIGN PATENT DOCUMENTS

| | | |
|---|---|---|
| EP | 0611569 | 1/1994 |
| GB | 2385768 A | 9/2003 |
| JP | 2001-270832 A2 | 10/2001 |
| JP | 2005-065525 A2 | 3/2005 |
| JP | 2009-538900 T | 11/2009 |
| WO | WO 97/48388 | 12/1997 |
| WO | WO 00/62812 | 10/2000 |
| WO | WO 01/17517 | 3/2001 |
| WO | WO 02/01969 | 1/2002 |
| WO | WO 02/20028 | 3/2002 |
| WO | WO 02/092779 | 11/2002 |
| WO | WO 2005/004630 | 1/2005 |
| WO | WO 2005/006877 | 1/2005 |

OTHER PUBLICATIONS

"Antioxidants Effect of Various Rosemary Clones," Acta Biologica Szegediensis, vol. 47 (104), pp. 111-113, 2003.
Shields, "Chicken Inherently Contains Lysine"; OBYGN.net; col. 5, line 20; col. 6, line 15; 2000.
Ping et al. "Blueberries Extract Supplementation Improves Physical Performance and Decreases Oxidative Stress in Mice", Bull. Exp. Biol. Med., vol. 3, pp. 249-251, 2004.
Lal, et al., "Efficacy of Curcumin in the Management of Chronic Anterior Uveitis", Phytotherapy Research, vol. 13, pp. 318-322, 1999.
Ursini et al., "A Novel Antioxidant Flavanoid (IdB 1031) Affecting Molecular Mechanisms of Cellular Activation", Biochem. Pharmacol., vol. 25, pp. 2505-2513, 1976.
White et al., "Does Turmeric Relieve Inflammatory Conditions?" The Journal of Family Practice, vol. 60, No. 3, pp. 155-156, Mar. 2011.
Cervellati et al., "Evaluation of Antioxidant Activity of Some Natural Polyphenolic Compounds Using the Briggs-Rauscher Reaction Method", Journal of Agriculture and Food Chemistry, vol. 50, pp. 7504-7509, Nov. 21, 2002.
Zhang, et al., "Effect of caffeic acid, seopelotin and scutellarin on rat retinal neurons in vitro", Zhongguo Zhongyao Zazhi 30(12):907-9, Jun. 2005—Abstract.
Al-Sereiti, et al., "Pharmacology of rosemary (*Rosmarinus officinalis* Linn.) and its therapeutic potentials", Ind. J. Exp. Biol., 37:124-130, 1999.
Rababah et al., "Total Phenolics and Antioxidant Activities of Fenugreek, Green Tea, Black Tea, Grape Seed, Ginger, Rosemary, Gotu Kola, and Ginkgo Extracts, Vitamin E and tert-Butylhydroquinone", J. Agric. Food Chem, vol. 52, pp. 5183-5186, 2004.
Cabrera et al., "Beneficial Effects of Green Tea—A Review", Journal of the American College of Nutrition, vol. 25, No. 2, pp. 79-99, 2006.
Liebert et al., "Antioxidant Properties and Total Phenolies Content of Green and Black Tea Under Different Brewing Conditions", Z. Lebensm Unters Forsch A. vol. 208, pp. 217-220, 1999.

*Primary Examiner* — Michael Meller

(74) *Attorney, Agent, or Firm* — Amy M. Foust

(57) ABSTRACT

The present invention relates to a method for promoting eye health by administering to a companion animal a composition comprising at least one polyphenol selected from the group consisting of rosemary, rosemary extract, coffeic acid, coffee extract, turmeric extract, cucurmin, blueberry extract, grapeseed extract, rosemarinic acid, tea extract, and mixtures thereof.

19 Claims, No Drawings

METHOD FOR PROMOTING EYE HEALTH

CROSS REFERENCE TO RELATED APPLICATIONS

This application claims the benefit of U.S. patent application Ser. No. 11/810,893, filed Jun. 7, 2007; which claims priority to U.S. Provisional Application No. 60/811,857, filed Jun. 8, 2006.

FIELD OF THE INVENTION

The present invention relates to a method for promoting eye health in a companion animal comprising: administering to a companion animal a composition comprising at least one polyphenol selected from the group consisting of rosemary, rosemary extract, coffeic acid, coffee extract, turmeric extract, cucurmin, blueberry extract, grapeseed extract, rosemarinic acid, tea extract, and mixtures thereof.

BACKGROUND OF THE INVENTION

Vision loss in companion animals is often related to free radical damage to the companion animal lens and corneal epithelial cells, environmental stress such as sunlight, and the normal stress associated with aging of the companion animal. A free radical is a highly reactive molecule that binds to and destroys body components. As a result of the companion animal's eye reliance on light to function properly, the eyes are particularly vulnerable to free radical attacks. While light aids a companion animal on its ability to see, light also creates additional free radicals that enhance vision loss by promoting cell and membrane damage of the companion animal eyes.

Blue light (400-500 nm) of the visible spectrum has a relatively high energy, can penetrate tissue(s) and has been shown to have a major impact on photoreceptor and retinal epithelial cell function, inducing photochemical damage and apoptotic cell death. The blue light comes from the glaring snow or water reflex and can be a hazard to sporting, hunting, working, rescuing and fishing dogs. Exposure to visible blue light causes an increase in both mitochondrial and nuclear DNA lesions and an increase in free radical production in retinal epithelial cells. Blue light induced free radical damage to the mitochondria can be blocked either by inhibiting the mitochondrial electron transport chain or by mitochondria-specific antioxidants.

Additionally, as the companion animal ages, free radicals participate in the aging in the companion animal eye. Cataract formation which is thought to be triggered by the free radical stress on the companion eye is primarily associated with advancing age of the companion animal.

There still exists a need for a composition that treats and aids in promoting eye health of a companion animal.

It is therefore an object of the present invention to provide method of improving eye health in a companion animal comprising administering a composition that prevents or treats environmental stress, prevents or treats age associated stress, slows down cataract progression, improves vision, and maintains younger eyes in the companion animal.

SUMMARY OF THE INVENTION

The present invention relates to a method for promoting eye health in a companion animal comprising: administering to a companion animal a composition comprising at least one polyphenol selected from the group consisting of rosemary, rosemary extract, coffeic acid, coffee extract, turmeric extract, cucurmin, blueberry extract, grapeseed extract, rosemarinic acid, tea extract, and mixtures thereof.

The present invention is also directed to non-limiting methods of preparing the composition as described above.

DETAILED DESCRIPTION OF THE INVENTION

The composition of the present invention comprises at least one polyphenol selected from the group consisting of rosemarinic acid, rosemary extract, coffeic acid, coffee extract, turmeric extract, cucurmin, blueberry extract, grapeseed extract, rosemarinic acid, tea extract, and mixtures thereof.

These and other limitations of the compositions and methods of the present invention, as well as many of the optional ingredients suitable for use herein, are described in detail hereinafter.

As used herein, the term "adapted for use" means that the composition described can meet the American Association of Feed Control Officials (AAFCO) safety requirements for providing animal food products for an animal as may be amended from time to time.

As used herein, the term "companion animal" means an animal preferably including (for example) dogs, cats, kitten, puppy, senior dog, senior cat, adult dog, adult cat, horses, cows, pigs, rabbits, guinea pig, hamster, gerbil, ferret, horses, zoo mammals and the like. Dogs, cats, kitten, puppy, senior dog, senior cat, adult dog, adult cat are particularly preferred.

As used herein, the term "Adult" or the like is a companion animal which is from about 3 years old to about 6 years old. An adult dog is a domestic dog at the age of at least about 3; and an adult cat is a domestic cat at the age of at least about 3.

As used herein, the term "composition" means a composition that can be ingested by a companion animal, supplements for a companion animal, pet food, dog food, cat food, treats, biscuits, raw hide, treats, chews, fillers, gravy, sauce, beverage, supplemental water, and combinations thereof. The composition can be wet, moist, and/or dry.

The term "complete and nutritionally balanced" as used herein, unless otherwise specified, refers to a composition having all known required nutrients in proper amounts and proportions based upon the recommendation of recognized authorities in the field of animal nutrition.

As used herein, the term "kitten" refers to a domestic cat which is about 3 years old or less, alternately about 2 years old or less, alternately about 1 year old or less.

As used herein, the term "polyphenol" means a group of plant chemical substances, characterized by the presence of more than on phenol group per molecule. The polyphenols can be responsible for the coloring or aroma of some plants. Polyphenols are powerful antioxidants with potential health benefits including antiviral, antibacterial, anti-inflammatory, anticarcinogenic, anti-aging (neurodegenerative) effects and combinations thereof.

As used herein, the term "puppy" refers to a domestic dog which is about 3 years old or less, alternately about 2 years old or less, alternately about 1 year old or less.

As used herein, the term "Senior" or the like is a companion animal which is considered middle-aged or older in accordance with standards commonly utilized in the art, with the following proviso: a senior dog is a domestic dog at the age of at least about 6; and a senior cat is a domestic cat at the age of at least about 6. If the senior dog is a large breed dog, meaning a dog weighing more than 50 pounds, the senior dog is a domestic dog at the age of at least about 5.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The composition and methods of the present invention can comprise, consist of, or consist essentially of, the essential elements and limitations of the invention described herein, as well as any additional or optional ingredients, components, or limitations described herein or otherwise useful in compositions intended for companion animal consumption.

Method

The present invention is a method for promoting eye health in a companion animal comprising: administering to a companion animal a composition comprising at least one polyphenol selected from the group consisting of rosemary, rosemary extract, coffeic acid, coffee extract, turmeric extract, cucurmin, blueberry extract, grapeseed extract, rosemarinic acid, tea extract, and mixtures thereof. Eye health can include preventing or treating environmental stress, preventing or treating age associated stress, slow down cataract progression, improve vision, and maintain younger eyes in the companion animal.

Product Form

The compositions are adapted for use by companion animals. The composition of the present invention is preferably administered to promote eye health. The composition of the present invention can be a moist composition (i.e. those having a total moisture content of from about 16% to 50%, by weight of the product), and/or a wet composition (i.e. those having a total moisture content of greater than 50%, by weight of the product), and/or dry composition (i.e. those having a total moisture content of from about 0% to about 16%, by weight of the product). Unless otherwise described herein, wet composition, moist composition and/or dry composition are not limited by their composition or method of preparation.

The composition herein can be complete and nutritionally balanced. A complete and nutritionally balanced animal food composition may be compounded to be fed as the sole ration and is capable of maintaining the life and/or promote reproduction without any additional substance being consumed, except for water.

The composition and components of the present invention are selected for consumption by an animal and are not intended for consumption by humans. Non-limiting examples of compositions include supplements for an animal, pet food, dog food, cat food, treats, biscuits, raw hide, treats, chews, fillers gravy, sauce, beverage, supplemental water, and combinations thereof.

Additionally, administration in accordance with the present invention may be continuous or intermittent, depending, for example, upon the recipient's physiological condition, whether the purpose of the administration is therapeutic or prophylactic, and other factors known to skilled practitioners.

Polyphenol

The composition comprises at least one polyphenol. The polyphenol is selected from the group consisting of rosemary extract, rosemarinic acid, coffee extract, coffeic acid, turmeric extract, blueberry extract, grapeseed extract, tea extract, and mixtures thereof.

The composition comprising on a dry matter basis from about 0.01% of said polyphenol to about 90% of said polyphenol, by weight of the composition. The composition comprising on a dry matter basis from about 0.1% of said polyphenol to about 35% of said polyphenol, from about 1% of said polyphenol to about 15% of said polyphenol, from about 1% of said polyphenol to about 10% of said polyphenol, from about 3% of said polyphenol to about 10% of said polyphenol, by weight of the composition.

The use of polyphenol has proved to be beneficial for promoting eye health of the companion animal. Polyphenols have antioxidants activity to prevent photo-oxidative stress or free radical damage to lens cellular DNA, protein and lipids and anti-inflammatory effect to protect the lens from inflammation. Polyphenols have anti-hyperglycemic effect and will attenuate the eye lens damage associated with the diabetic condition. In addition, polyphenols have protein or proteoglycan-binding properties to lower intraocular pressure and release eye discomfort.

Rosemary Extract

Rosemary extract is a polyphenol. Constituents of rosemary or rosemary extract are coffeic acid and its derivatives such as rosemarinic acid. These compounds have antioxidant activity and anti-inflammatory effect. Coffeic acids prevent posterior capsule opacification by suppressing the transformation of the lens epithelial cells.

Nonlimiting sources of rosemary extract for use in the present invention are rosemary.

When rosemary extract is present, the composition comprises on a dry matter basis from about 0.01% of said rosemary extract to about 90% of said rosemary extract, by weight of the composition. The composition comprising on a dry matter basis from about 0.1% of said rosemary extract to about 35% of said rosemary extract, from about 1% of said rosemary extract to about 15% of said rosemary extract, from about 1% of said rosemary extract to about 10% of said rosemary extract, from about 3% of said rosemary extract to about 10% of said rosemary extract, by weight of the composition.

When rosemarinic acid is present, the composition comprises on a dry matter basis from about 0.01% of said rosemarinic acid to about 90% of said rosemarinic acid, by weight of the composition. The composition comprising on a dry matter basis from about 0.1% of said rosemarinic acid to about 35% of said rosemarinic acid, from about 1% of said rosemarinic acid to about 15% of said rosemarinic acid, from about 1% of said rosmarinic acid to about 10% of said rosemarinic acid, from about 3% of said rosemarinic acid to about 10% of said rosemarinic acid, by weight of the composition.

Coffee Extract

Coffee extract is a polyphenol. The main constituent of coffee extract is coffeic acid and is believed to display antioxidant activity and may prevent or treat cataracts.

When coffee extract is present, the composition comprises on a dry matter basis from about 0.01% of said coffee extract to about 90% of said coffee extract, by weight of the composition. The composition comprising on a dry matter basis from about 0.1% of said coffee extract to about 35% of said coffee extract, from about 1% of said coffee extract to about 15% of said coffee extract, from about 1% of said coffee extract to about 10% of said coffee extract, from about 3% of said coffee extract to about 10% of said coffee extract, by weight of the composition.

When coffee extract is present nonlimiting sources of coffee extract include coffee bean, coffee, coffee berry, coffee fruits. When coffeic acid is present nonlimiting sources of coffeic acid include tea, berries, coffee bean, coffee, coffee berry, coffee fruits, rosemary extract, and/or grapes extract.

When coffeic acid is present, the composition comprises on a dry matter basis from about 0.01% of said coffeic acid to about 90% of said coffeic acid, by weight of the composition. The composition comprising on a dry matter basis from about 0.1% of said coffeic acid to about 35% of said coffeic acid, from about 1% of said coffeic acid to about 15% of said coffeic acid, from about 1% of said coffeic acid to about 10% of said coffeic acid, from about 3% of said coffeic acid to about 10% of said coffeic acid, by weight of the composition.

Turmeric Extract

Turmeric extract is a polyphenol. Turmeric extract is a spice which comprises a main active compound that is curcumin. Curcumin is a bioactive polyphenol plant pigment. It is believed that curcumin has antioxidant activity by scavenging reactive oxygen species and enhancing antioxidant enzyme GSH and GST activity and inhibiting lipid and protein oxidation. Therefore, cucurmin prevents lipid peroxidation and protein aggregation and provides a delay in the progression and maturation of cataracts. In addition cucurmin can minimize osmotic stress associated with diabetic cataract.

Nonlimiting source of turmeric extract for use in the present invention is tumeric.

When turmeric extract is present, the composition comprises on a dry matter basis from about 0.01% of said turmeric extract to about 90% of said turmeric extract, by weight of the composition. The composition comprising on a dry matter basis from about 0.1% of said turmeric extract to about 35% of said turmeric extract, from about 1% of said turmeric extract to about 15% of said turmeric extract, from about 1% of said turmeric extract to about 10% of said turmeric extract, from about 3% of said turmeric extract to about 10% of said turmeric extract, by weight of the composition.

Blueberry Extract

Blueberry extract is a polyphenol. The blueberry extract is rich in anthocyanins which display antioxidant activity by quenching singlet oxygen and therefore preventing the photooxidation of pigment.

Nonlimiting source of blueberry extract for use in the present invention is blue berry.

When blueberry extract is present, the composition comprises on a dry matter basis from about 0.01% of said blueberry extract to about 90% of said blueberry extract, by weight of the composition. The composition comprising on a dry matter basis from about 0.1% of said blueberry extract to about 35% of said blueberry extract, from about 1% of said blueberry extract to about 15% of said blueberry extract, from about 1% of said blueberry extract to about 10% of said blueberry extract, from about 3% of said blueberry extract to about 10% of said blueberry extract, by weight of the composition.

Grapeseed Extract

Grapeseed extract is a polyphenol. The grape seed extract is rich in procyanidins which display antioxidant activity. The grape seed extract comprises about 38.5% procyanindins. Procyanidins and their antioxidative metabolites help prevent the progression of cataract formation by their antioxidative action, such as preventing the lens and retinal microvasculature LDL oxidation. Procyanidins may also have vitamin E-sparing effect.

Nonlimiting source of grapeseed extract for use in the present invention is grape seed.

When grapeseed extract is present, the composition comprises on a dry matter basis from about 0.01% of said grapeseed extract to about 90% of said grapeseed extract, by weight of the composition. The composition comprising on a dry matter basis from about 0.1% of said grapeseed extract to about 35% of said grapeseed extract, from about 1% of said grapeseed extract to about 15% of said grapeseed extract, from about 1% of said grapeseed extract to about 10% of said grapeseed extract, from about 3% of said grapeseed extract to about 10% of said grapeseed extract, by weight of the composition.

Tea Extract

Tea extract is a polyphenol. The tea extract has antioxidant activity so as to quench reactive oxygen species such as singlet oxygen, superoxide and hydroxyl radicals. This quenching prevents the oxidative cross-linking of test proteins and inhibit single strand breakage of DNA in whole cells; enhance antioxidant defense system by preserving antioxidant enzyme activity; inhibit lens epithelial cell proliferation by inducing apoptosis and improve glucose metabolisms.

Nonlimiting sources of tea extract for use in the present invention are black tea, white tea, oolong tea, and/or green tea.

When tea extract is present, the composition comprises on a dry matter basis from about 0.01% of said tea extract to about 90% of said tea extract, by weight of the composition. The composition comprising on a dry matter basis from about 0.1% of said tea extract to about 35% of said tea extract, from about 1% of said tea extract to about 15% of said tea extract, from about 1% of said tea extract to about 10% of said tea extract, from about 3% of said tea extract to about 10% of said tea extract, by weight of the composition.

The polyphenol utilized in accordance with the present invention can additionally be formulated as a pharmaceutical, and/or veterinary composition and administered to an animal in a variety of forms adapted to a chosen route of administration, for example, orally, parenterally, intravenously, subcutaneously, and like routes. A preferred method of administration is oral administration.

Carotenoids

The composition of the present invention can comprise a carotenoid. A "carotenoid" is a class of pigments occurring in the tissues of higher plants, algae, bacteria and fungi. They are usually yellow to deep red, crystalline solids, soluble in fats and oils, insoluble in water, highmelting, stable to alkali, unstable to acids and oxidizing agents, their color is easily destroyed by hydrogenation or by oxidation, and some are optically active. Carotenoids are natural pigments synthesized by plants and microorganisms that are thought to function as light absorbing pigments during photosynthesis and to protect cells from photosensitization. Structurally, carotenoids consist of eight isoprenoid units joined so that their arrangement is reversed at the center of the molecule. Carotenoids have demonstrated biological activities in addition to maintaining oxidative balance. Carotenoid structure strongly affects the physical properties, chemical reactivity and biologic functions of these compounds. It has been suggested that the size, shape, hydrophobicity and polarity of individual carotenoids may dramatically affect the bioavailability, absorption, circulation, tissue and subcellular distribution and excretion in mammals.

When a carotenoid is present, the carotenoid is selected from the group consisting of lutein, astaxanthin, zeaxanthin, bixin, lycopene, and mixtures thereof.

Lutein is an antioxidant, belonging to a class of lipid-soluble yellow-to-red pigments known as carotenoids. Lutein and zeaxanthin are structural isomers of one another. Lutein can be extracted in crystalline form from marigolds. Dietary sources of lutein include mustard greens, spinach, kale, broccoli, leaf lettuce, green peas, brussel sprouts, corn, some squash and green beans. Lutein is powerful antioxidant believed to protect the body and eyes from damaging free radicals. It is the main carotenoid found in the retina of the eye, and may be effective in the treatment of cataracts. It works extremely well against sunlight damage, and Lutein may decrease the occurrence of macular degeneration by more than 50%. The composition of the present invention may comprise at least about 0.01% of lutein, by weight of the composition, from about 0.01% to about 20%, by weight of the composition, from about 0.05% to about 10%, by weight of the composition.

Zeaxanthin is an antioxidant, belonging to a class of lipid-soluble yellow-to-red pigments known as carotenoids. Zeaxanthin can be extracted in crystalline form from marigolds. Dietary sources of zeaxanthin include mustard greens, spinach, kale, broccoli, leaf lettuce, green peas, brussel sprouts, corn, some squash and green beans. Zeaxanthin is powerful antioxidant believed to protect the body and eyes from damaging free radicals. The composition of the present invention may comprise at least about 0.01% of zeaxanthin, by weight of the composition, from about 0.01% to 20.0%, by weight of the composition, from about 0.05% to about 10%, by weight of the composition.

Astaxanthin can be provided as free astaxanthin or as astaxanthin diester. Naturally produced astaxanthin can be obtained from fungi, crustaceans, and algae, e.g., *Haematococcus* sp. (e.g., as described in U.S. Pat. No. 5,744,502). Astaxanthin is also produced by wild-type and genetically engineered *Pfaffia* yeast, and is commercially available from Archer Daniels Midland Co.; Aquasearch Inc.; AstaCarotene AB; Cyanotech Corporation and Micro Gaia, Inc. Synthetically produced astaxanthin is also commercially available from Hoffman-LaRoche, Ltd. The composition of the present invention may comprise at least about 0.01% of Astaxanthin, by weight of the composition, from about 0.01% to about 20% of Astaxanthin, by weight of the composition, from about 0.05% to about 10% of Astaxanthin, by weight of the composition.

Bixin is naturally occurring carotenoid, found in the pulp of the *B. orellana* seed (also called annatto seed), used all over the world as a red-orange dye for coloring rice, cheeses, soft drinks, oil, butter, soup and cosmetics. As annatto extract, it is used as a color additive in food. Bixin can scavenge free radicals and prevent oxidative damage to DNA and lipid oxidation both in vitro and in vivo. Data also suggests that bixin has chemoprotective effect on colorectal cancer. The composition of the present invention may comprise at least about 0.01% of bixin, by weight of the composition, from about 0.01% to about 20%, by weight of the composition, from about 0.05% to about 10%, by weight of the composition.

Lycopene is an open-chain unsaturated carotenoid that imparts red color to tomatoes, guava, rosehip, watermelon and pink grapefruit. Lycopene is a proven antioxidant, which neutralize free radicals that may damage the body's cells, thereby conferring protection against prostate cancer, breast cancer, atherosclerosis and associated coronary artery disease. It reduces LDL oxidation and helps reduce cholesterol levels in the blood. In addition, preliminary research suggests that lycopene may reduce the risk of macular degenerative disease. The composition of the present invention may comprise at least about 0.01% of lycopene, by weight of the composition, from about 0.01% to about 20%, by weight of the composition, from about 0.05% to about 10%, by weight of the composition.

Amino Acids

The composition of the present invention can comprise an amino acid. Amino acids are the "building Blocks" of the body. Besides building cells and repairing tissue, they form antibodies to combat invading bacteria & viruses; they are part of the enzyme & hormonal system; they build nucleoproteins (RNA & DNA); they carry oxygen throughout the body and participate in muscle activity. When protein is broken down by digestion the result is 22 known amino acids. Eight are essential (cannot be manufactured by the body) the rest are non-essential (can be manufactured by the body with proper nutrition).

When an amino acid is present, the amino acid is selected from the group consisting of Lysine, Taurine, Histidine, Carnosine, Alanine, Cysteine, and mixtures thereof.

L-lysine is an essential amino-acid that has been shown to significantly reduce virus shedding in affected cats and decrease the duration of feline herpes virus-1 (FHV-1) infection, which is a very common infection in cats. FHV-1 is associated with many ocular diseases in cats including conjunctivitis, keratitis, corneal ulceration, symblepharon formation, L-lysine suppresses FHV-1 replication by competing with arginine for incorporation into the viral genome. The composition of the present invention may comprise at least about 0.05% of Lysine, by weight of the composition, from about 0.05% to about 10% of Lysine, by weight of the composition, from about 1.5% to about 5% of Lysine, by weigh of the composition.

Taurine is an amino acid used as a building block of all the other amino acids; it is found in the eye, heart muscle, white blood cells, skeletal muscle, and central nervous system. Taurine and sulfur are considered to be factors necessary for the control of many biochemical changes that take place in the aging process; aids in the clearing of free radical wastes. Taurine is a sulfur-containing amino acid that is essential to the cat because a cat has a limited ability to synthesize it from cysteine, which is a precursor amino acid in most animal species. Therefore cats have a nutritional requirement for taurine. Nutritional retinal degeneration and feline central retinal degeneration are identical and associated with taurine deficiency in cats. Taurine deficiency affects the cones in the retina, which are most prominent in the area centralis which is located dorsetemporal to the optic disc. The composition of the present invention may comprise at least about 0.05% of Taurine, by weight of the composition, from about 0.05% to about 10% of Taurine, by weight of the composition, from about 0.1% to about 5% of Taurine, by weight of the composition.

Histidine is found abundantly in hemoglobin. Histidine is a precursor of histamine, a compound released by immune system cells during an allergic reaction. Histidine is needed for growth and for the repair of tissue, as well as the maintenance of the myelin sheaths that act as protector for nerve cells. Histidine is further required for the manufacture of both red and white blood cells, and helps to protect the body from damage caused by radiation and in removing heavy metals from the body. The composition of the present invention may comprise at least about 0.05% of Histidine, by weight of the composition, from about 0.05% to about 10% of Histidine, by weight of the composition, from about 0.1% to about 5% of Histidine, by weight of the composition.

Carnosine has excellent potential to act as a natural antioxidant with hydroxyl radical, singlet oxygen scavenging and lipid peroxidase activities. A striking effect of carnosine is its demonstrated ability to prevent, or partially reverse, lens cataract. Carnosine protects the crystalline lens from oxidative stress-induced damage. Used together with vitamin E and other antioxidants, it has an optimum effect. It is believed that Carnosine may reduce the destruction of valuable proteins and DNA by sugar molecules, a process known as glycosylation. Carnosine may help prevent damage from glycosylation, ridding the system of any abnormal substances and leaving it free to function optimally. The composition of the present invention may comprise at least about 0.05% of Carnosine, by weight of the composition, from about 0.05% to about 10% of Carnosine, by weight of the composition, from about 0.1% to about 5% of Carnosine, by weight of the composition.

Alanine is a nonessential amino acid that can be manufactured by the companion animal from other sources as needed. Alanine is one of the simplest of the amino acids and is involved in the energy-producing breakdown of glucose. In conditions of sudden anaerobic energy need, when muscle proteins are broken down for energy, Alanine acts as a carrier molecule to take the nitrogen-containing amino group to the liver to be changed to the less toxic urea, thus preventing buildup of toxic products in the muscle cells when extra energy is needed. Alanine is found in a wide variety of foods, but is particularly concentrated in meats. The composition of the present invention may comprise at least about 0.05% of Alanine, by weight of the composition, from about 0.05% to about 10% of Alanine, by weight of the composition, from about 1% to about 5% of Alanine, by weight of the composition.

Cysteine functions as an antioxidant and is a powerful aid to the body in protecting against radiation and pollution. It can help slow down the aging process, deactivate free radicals, neutralize toxins; aids in protein synthesis and presents cellular change. The composition of the present invention may comprise at least about 0.05% of Cysteine, by weight of the composition, from about 0.05% to about 10% of Cysteine, by weight of the composition, from about 0.2% to about 5% of Cysteine, by weight of the composition.

Antioxidant

The composition of the present invention can comprise an antioxidant. An antioxidant is an enzyme or other organic molecule that can counteract the damaging effects of oxygen in tissues. Although the term technically applies to molecules reacting with oxygen, it is often applied to molecules that protect from any free radical. When an antioxidant is present, the antioxidant is selected from the group consisting of Vitamin E, Vitamin C, Vitamin A, CoQ10, and mixtures thereof.

Vitamin E is a lipid soluble compound and the most significant antioxidant activity of vitamin E is localized to cellular membranes. Vitamin E maintains oxidative balance by protecting cellular membranes from lipid peroxidation. Vitamin E is a lipid soluble antioxidant and provides defenses against cellular oxidative damage. All vitamin E in the companion animal is derived from the diet and includes multiple chemical forms. Major dietary sources of vitamin E are vegetable oils, margarine and shortening, with nuts, seeds, whole grains and wheat germ providing additional sources. "Vitamin E" includes eight different chemical forms: four tocopherols and four tocotrienols. The most biologically active form of vitamin E is alpha-tocopherol. Vitamin E is important in dogs. Phospholipids are a significant structural component of photoreceptors and normal shedding and phagocytosis by retinal pigment epithelium produces a peroxidized lipoprotein or lipofusin from the lysosomes in the cell. A deficiency in vitamin E may result in pathologic changes in the muscle, central nerve system, reproductive tract and retina. Ocular lesions such as cataracts, decreased vision to blindness and retinal degeneration occur with prolonged vitamin E deficiency in dogs. Vitamin E supplement retards the intracellular accumulation of oxidized lipoprotein or lipofusin pigment.

The composition of the present invention may comprise at least about 0.01% of Vitamin E, by weight of the composition, from about 0.01% to about 10% of Vitamin E, by weight of the composition, from about 0.2% to about 5% of Vitamin E, by weight of the composition.

Vitamin C (as calcium ascorbate) is a water-soluble, found in aqueous cellular compartments and is a line of defense against direct free radical exposure (e.g., radiation, sunlight). Vitamin C maintains oxidative balance by effectively scavenging free radicals produced in the aqueous cellular cytoplasm and by recycling (protecting) vitamin E in cellular membranes. The preferred form of Vitamin C is as calcium ascorbate. The chemical core of vitamin C is composed of a five-membered lactone ring containing a bifunctionalenediol group and an adjacent carbonyl group. Ascorbate is highly soluble in water. The unusual chemical structure, thermodynamic redox potential and rapid reaction kinetics observed for ascorbate support its unique role as the terminal small molecule antioxidant in biological systems. Ascorbic acid (ASC) exists in three different redox states in biological systems: ASC, semidehydroascorbate (SDA), and dehydroascorbate (DHA). DHA is formed as the result of two consecutive and reversible, one-electron oxidation processes. Because the unpaired electron is in a highly delocalized .pi.-system, the ascorbate radical is relatively unreactive. Thus, the thermodynamics and kinetics of ascorbate chemistry make ASC a superior biological donor antioxidant. SDA and DHA are recycled via reduction back to ascorbate by endogenous enzyme systems. It is believed that ascorbate enhances the antioxidant action of vitamin E by reducing reduction of the tocopheroxyl radical. The reactions between the tocopheroxyl radical and ascorbate provide a mechanism for exporting oxidative free radicals away from the cellular membranes. In essence, tocopherols protect membranes by stopping propagation reactions of lipid peroxy radicals and ascorbate acts by protecting the membrane against possible damage from the tocopheroxyl radical. Thus, ascorbate helps to maintain oxidative balance by scavenging free radicals and recycling the useful forms of other antioxidants, such as vitamin E.

The composition of the present invention may comprise at least about 0.01% of Vitamin C, by weight of the composition, from about 0.01% to about 10% of Vitamin C, by weight of the composition, from about 0.2% to about 5% of Vitamin C, by weight of the composition.

Vitamin A and carotene can be obtained from either animal or vegetable sources. The animal form is divided between retinol and dehydroretinol whereas the vegetable carotene can be split into four very potent groups—alpha-carotene, beta-carotene, gamma-carotene and crypto-carotene. Vitamin A is required for night vision. It assists the immune system, and because of its antioxidant properties is great to protect against pollution and other diseases. It is believed that Vitamin A helps slow aging. Vitamin A is required for development and maintenance of the epithelial cells, in the mucus membranes, and your skin, and is important in the formation of bone and teeth, storage of fat and the synthesis of protein and glycogen.

The composition of the present invention may comprise at least about 0.01% of Vitamin A, by weight of the composition, from about 0.01% to about 10% of Vitamin A, by weight of the composition, from about 0.2% to about 5% of Vitamin A, by weight of the composition.

Coenzyme Q10 is a powerful natural occurring compound, promoting chemical reactions, that aids in protecting the companion animal from free radicals, and is also called ubiquinone. Coenzyme Q10 (CoQ10) is naturally present in foods, and can be synthesized by the companion animal from the amino acid tyrosine during a multistage (17 stages) process requiring eight vitamins and several trace elements. Coenzyme Q10 provides antioxidant qualities as well as the control it exercises on the flow of oxygen within cells, assistance with cardiovascular functioning, the production of energy, assistance with absorption of other nutrients as well as its immune boosting properties. Coenzyme Q10 is the coenzyme for at least three mitochondrial enzymes as well as other enzymes in the cell. The mitochondrial function has played a central role in age related macular degeneration The composition of the present invention may comprise at least about 0.01% of Coenzyme Q10, by weight of the composition, from about 0.01% to about 10% of Coenzyme Q10, by weight of the composition, from about 0.2% to about 5% of Coenzyme Q10, by weight of the composition.

Compositions

It is anticipated that the polyphenol described in the present invention can be added to any composition adapted for administration to a companion animal.

Typical formulae for compositions are well known in the art. In addition to proteinaceous and farinaceous materials, the compositions of the invention generally may include vitamins, minerals, and other additives such as flavorings, preservatives, emulsifiers and humectants. The nutritional balance, including the relative proportions of vitamins, minerals, protein, fat and carbohydrate, is determined according to dietary standards known in the veterinary and nutritional art.

Nonlimiting examples of dry compositions may optionally contain on a dry matter basis, from about 1% to about 50% crude protein, from about 0.5% to about 25% crude fat, from about 1% to about 10% supplemental fiber, and from about 1% to about 30% moisture, all by weight of the composition. Alternatively, a dry composition may contain on a dry matter basis, from about 5% to about 35% crude protein, from about 5% to about 25% crude fat, from about 2% to about 8% supplemental fiber, and from about 2% to about 20% moisture, all by weight of the composition. Alternatively, the dry composition contains on a dry matter basis, a minimum protein level of about from about 9.5% to about 22%, a minimum fat level of from about 8% to about 13%, a minimum moisture level of from about 3% to about 8%, a minimum supplemental fiber level of from about 3% to about 7%, all by weight of the composition. The dry composition may also have a minimum metabolizable energy level of about 3.5 Kcal/g.

Nonlimiting examples of a moist composition may optionally contain on a dry matter basis, from about 0.5% to about 50% crude protein, from about 0.5% to about 25% crude fat, from about 0.5% to about 15% supplemental fiber, from about 30% to about 50% moisture, all by weight of the composition. Alternatively, the moist compositions may contain on a dry matter basis, from about 5% to about 35% crude protein, from about 5% to about 25% crude fat, from about 1% to about 5% supplemental fiber, and from about 35% to about 45% moisture, all by weight of the composition. Alternatively, the moist composition may have on a dry mater basis, a minimum protein level of about from about 9.5% to about 22%, a minimum fat level of from about 8% to about 13%, a minimum moisture level of about 38% to about 42%, a minimum supplemental fiber level of from about 2% to about 3%, all by weight of the composition. The moist composition may also have a minimum metabolizable energy level of about 3.5 Kcal/g and from about 0.1% to about 20% ash.

Nonlimiting examples of a wet composition may optionally contain on a dry matter basis, from about 0.5% to about 50% crude protein, from about 0.5% to about 25% crude fat, from about 0.01% to about 15% supplemental fiber, from about 50% to about 90% moisture, all by weight of the composition. Alternatively, the wet compositions may contain on a dry matter basis, from about 5% to about 35% crude protein, from about 5% to about 25% crude fat, from about 0.05% to about 5% supplemental fiber, and from about 60% to about 85% moisture, all by weight of the composition. Alternatively, a wet composition may contain on a dry matter basis, a minimum protein level of about from about 9.5% to about 22%, a minimum fat level of from about 8% to about 13%, a moisture level of from about 65% to about 80%, a minimum supplemental fiber level of from about 0.1% to about 3%, all by weight of the composition. The wet composition may also have a minimum metabolizable energy level of about 1.0 Kcal/g and from about 0.1% to about 20% ash.

In one embodiment of the present invention, the composition is an composition, whether dry, moist, wet, or otherwise, that comprises on a dry matter basis, from about 5% to about 50%, alternatively 20% to about 50% of animal-derived ingredients, by weight of the composition. Non-limiting examples of animal-derived ingredients include chicken, beef, pork, lamb, turkey (or other animal) protein or fat, egg, fishmeal, and the like.

Where the composition is in the form of a gravy, the composition may comprise at least 10% of a broth, or stock, non-limiting examples of which include vegetable beef, chicken or ham stock. Typical gravy compositions may comprise on a dry matter basis, from about 0.5% to about 5% crude protein, and from about 2% to about 5% crude fat.

Where the composition is in the form of a supplement composition such as biscuits, chews, and other treats, the supplement may comprise, on a dry matter basis, from about 20% to about 60% protein, from about 22% to about 40% protein, by weight of the supplement composition. As another example, the supplement compositions may comprise, on a dry matter basis, from about 5% to about 35% fat, or from about 10% to about 30% fat, by weight of the supplement composition.

Optional Ingredients

The composition of the present invention can further comprise a wide range of other optional ingredients.

Nonlimiting examples of additional components include animal protein, plant protein, farinaceous matter, vegetables, fruit, egg-based materials, undenatured proteins, food grade polymeric adhesives, gels, polyols, starches, gums, flavorants, seasonings, salts, colorants, time-release compounds, minerals, vitamins, antioxidants, prebiotics, probiotics, aroma modifiers, textured wheat protein, textured soy protein, textured lupin protein, textured vegetable protein, breading, comminuted meat, flour, comminuted pasta, water, and combinations thereof.

Nonlimiting examples of optional ingredients can include at least one vegetable. Nonlimiting examples of vegetables include carrots, peas, potatoes, cabbage, celery, beans, corn, tomatoes, broccoli, cauliflower, leeks and combinations thereof.

Also useful herein, as an optional ingredient, is a filler. The filler can be a solid, a liquid or packed air. The filler can be reversible (for example thermo-reversible including gelatin) and/or irreversible (for example thermo-irreversible including egg white). Nonlimiting examples of the filler include gravy, gel, jelly, aspic, sauce, water, air (for example including nitrogen, carbon dioxide, and atmospheric air), broth, and combinations thereof.

Nonlimiting examples of colorants include, but are not limited to, synthetic or natural colorants, and any combination thereof. When present the colorants are from about 0.0001% to about 5%, more from about 0.001% to about 1%, even more from about 0.005% to about 0.1%, on a dry matter basis, of said colorant.

Additionally, probiotic microorganisms, such as Lactobacillus or Bifidobacterium species, for example, may be added to the composition or the animal food compositions themselves.

Also useful herein, as an optional ingredient, is at least one fruit. Nonlimiting examples include tomatoes, apples, avocado, pears, peaches, cherries, apricots, plums, grapes, oranges, grapefruit, lemons, limes, cranberries, raspberries, blueberries, watermelon, cantaloupe, mushmellon, honeydew melon, strawberries, banana, and combinations thereof.

The composition may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids (EPA) and docosahexanoic acid (DHA). The DHA level is at least about 0.05%, alternatively at least about 0.1%, alternatively at least about 0.15% of the animal food composition, all on a dry matter basis. The EPA level is at least about 0.05%, alternatively at least about 0.1%, alternatively at least about 0.15% of the animal food composition, all on a dry matter basis.

The compositions of the present invention may further comprise a source of carbohydrate. Grains or cereals such as rice, corn, milo, sorghum, barley, wheat, and the like are illustrative sources.

The compositions may also contain other materials such as dried whey and other dairy by products.

Method of Manufacture

The composition of the present invention may be prepared by any known or otherwise effective technique, suitable for making and formulating the desired composition. It is effective to manufacture the composition comprising the process of:
(a) receiving a commercially prepared or purchased polyphenol;
(b) combining by weight the polyphenol with additional ingredients;
(c) blending the polyphenaol with additional ingredients; and
(d) processing the polyphenol and additional ingredients to form a composition.

The composition can be processed by a variety of well-known means including steam tunnel, extrusion, freeze-texturization, baking, gelling, retort, microwave heating, ohmic heating, and combinations thereof.

Total Moisture Content Method

The method involves the analysis of the total moisture content in the composition. The analysis is based on the procedure outlined in AOAC method 930.15 and AACC method 44-19.

A composition sample is prepared by taking one unit volume, for example, 375 gram of the composition, and homogenizing in a food processor to a uniform consistency like a paste. A composition larger than 375 gram would be subdivided to create equal and representative fractions of the whole such that a 375 gram sample is obtained.

The paste of the composition is individually sampled in triplicate at a volume less than or equal to 100 ml and placed individually sealed in a 100 ml Nasco Whirl-Pak® (Fort Atkinson, Wis. 53538-0901). During the process of sealing the Whirl-Pak®, excess air is evacuated manually from the container just prior to final closure thereby minimizing the container headspace. The Whirl-Pak® is closed per manufacturer's instructions—tightly folding the bag over three (3) times and bending the tabs over 180 degrees.

All samples are refrigerated at 6° C. for less than 48 h prior to moisture analysis.

For total moisture analysis, the tare weight of each moisture tin and lid are recorded to 0.0001 g. Moisture tins and lids are handled using dry and clean forceps. Moisture tins and lids are held dry over desiccant in a sealed desiccator. A Whirl-Pak® containing a sample is unfolded and a 2.0000+/− 0.2000 gram sample is weighed into the uncovered moisture tin. The weight of the sample in the moisture tin is recorded. The lid is placed atop the moisture tin in an open position to allow moisture loss but contain all other material during air oven drying. The lid and moisture tin loaded with sample are placed in an air oven operating at 135° C. for 6 h. Time is tracked using a count-down timer.

After drying, the tin is removed from the oven and the dried lid is placed atop the tin using forceps. The covered moisture tin with dried sample is placed immediately in a desiccator to cool. The sealed desiccator is filled below the stage with active desiccant. Once cool to room temperature, the covered moisture tin with dried sample is weighed to 0.0001 g and weight recorded. The total moisture content of each sample is calculated using the following formula:

Total Moisture Content (%)=100−(weight of tin, lid and sample after drying−empty tin and lid weight)×100/initial sample weight.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention. All of the following examples are composition that are utilized by a companion animal.

Examples 1-6

| | Dry compositions | | | | | |
| --- | --- | --- | --- | --- | --- | --- |
| | Percentage % on dry matter basis (w/w) | | | | | |
| Ingredient | Example 1 | Example 2 | Example 3 | Example 4 | Example 5 | Example 6 |
| Chicken products and meals | 20 | 42 | 45 | 53 | 51 | 37 |

-continued

Dry compositions

Percentage % on dry matter basis (w/w)

| Ingredient | Example 1 | Example 2 | Example 3 | Example 4 | Example 5 | Example 6 |
|---|---|---|---|---|---|---|
| Cereal grains | 57.8 | 30.2 | 37.7 | 25.5 | 21.8 | 20 |
| Fat | 2.6 | 5.8 | 7 | 6 | 6 | 7 |
| Egg product | 3.45 | 2 | 3 | 2 | 2 | 2 |
| Vitamins | 0.15 | 0.4 | 0.6 | 0.8 | 0.4 | 0.4 |
| Minerals | 0.15 | 0.8 | 0.4 | 0.8 | 0.8 | 0.6 |
| Fiber | 3 | 5.9 | 6 | 7.05 | 7 | 7 |
| Rosemary extract | 0.0 | 0.01 | 0.1 | 1.0 | 10.0 | 25.0 |
| Rosemarinic acid | 0.0 | 0.0 | 0.0 | 0.0 | 0.0 | 1.0 |
| Coffee extract | 0.0 | 0.0 | 0.1 | 0.0 | 0.0 | 0.0 |
| Coffeic acid | 0.0 | 0.0 | 0.01 | 0.0 | 0.0 | 0.0 |
| Turmeric extract | 0.0 | 0.0 | 0.0 | 0.0 | 1.0 | 0.0 |
| Cucurmin | 0.0 | 0.0 | 0.0 | 0.0 | 0.01 | 0.0 |
| Blueberry extract | 10.0 | 0.0 | 0.0 | 0.0 | 0.0 | 0.0 |
| Grapeseed extract | 0.0 | 0.0 | 0.0 | 1.0 | 0.0 | 0.0 |
| Tea extract | 0.0 | 10.0 | 0.0 | 0.0 | 0.0 | 0.0 |
| Lutein | 0.05 | 0.1 | 0.1 | 0.05 | 0.0 | 0.0 |
| Lysine | 2.5 | 2.5 | 0.0 | 2.5 | 0.0 | 0.0 |
| Taurine | 0.3 | 0.3 | 0.0 | 0.3 | 0.0 | 0.0 |

The dry compositions of Examples 1, 2, 3, 4, 5 and 6 can be made by first, milling and mixing the cereal grains with vitamins and minerals and fiber sources and rosemary extract or rosemarinic acid or coffee extract or coffeic acid or turmeric extract or cucurmin or blueberry extract or grapeseed extract or tea extract, lutein, lysine and taurine. Then, add the cereal grains to the meat products and other protein sources. Extrude the ingredients into kibbles. Dry the kibbles. Package the finished product.

Examples 7-12

The wet compositions of Examples 7, 8, 9, 10, 11 and 12 can be made by first drying and milling cereal grains. Mix dried cereal grains, vitamins, minerals and fiber sources and rosemary extract or rosemarinic acid or coffee extract or coffeic acid or turmeric extract or cucurmin or blueberry extract or grapeseed extract or tea extract, lutein, lysine and taurine. Blend dry ingredients with meat products and other protein sources. The mixture is packaged into cans and cooked via retort process to provided finished product. For preformed pieces (chunks in gravy) mixture is extruded, passed through a steam tunnel for preconditioning, cut to desired shape, packaged with added water and retorted to provide safe finished product.

Wet compositions

Percentage % on dry matter basis (w/w)

| Ingredient | Example 7 | Example 8 | Example 9 | Example 10 | Example 11 | Example 12 |
|---|---|---|---|---|---|---|
| Chicken products and meals | 75.2 | 18.5 | 34 | 54 | 41 | 2 |
| Cereal grains | 4 | 19.4 | 17 | 19.6 | 8.7 | 1.5 |
| Egg product | 2.5 | 2 | 3 | 2 | 2 | 3.4 |
| Vitamins | 0.08 | 0.4 | 0.6 | 0.8 | 0.4 | 0.05 |
| Minerals | 0.12 | 0.8 | 0.4 | 0.8 | 0.4 | 0.15 |
| Fiber | 3 | 6 | 4.9 | 0 | 2.5 | 0 |
| Rosemary extract | 0.1 | 30.0 | 5.0 | 15.0 | 0.0 | 75.0 |
| Rosemarinic acid | 0.0 | 0.0 | 0.0 | 0.0 | 0.0 | 0.1 |
| Coffee extract | 0.0 | 0.0 | 5.0 | 0.0 | 0.0 | 0.0 |
| Coffeic acid | 0.0 | 0.0 | 0.1 | 0.0 | 0.0 | 0.0 |
| Turmeric extract | 0.0 | 5.0 | 0.0 | 0.0 | 0.0 | 0.0 |
| Cucurmin | 0.0 | 0.1 | 0.0 | 0.0 | 0.0 | 0.0 |
| Blueberry extract | 0.0 | 0.0 | 0.0 | 0.0 | 15.0 | 0.0 |
| Grapeseed extract | 0.0 | 0.0 | 0.0 | 5.0 | 0.0 | 0.0 |
| Tea extract | 15.0 | 0.0 | 0.0 | 0.0 | 0.0 | 0.0 |
| Lutein | 0.0 | 15.0 | 30.0 | 0.0 | 30.0 | 15.0 |
| Lysine | 0.0 | 2.5 | 0.0 | 2.5 | 0.0 | 2.5 |
| Taurine | 0.0 | 0.3 | 0.0 | 0.3 | 0.0 | 0.3 |

Examples 13-18

| | Moist compositions ||||||
| | Percentage % on dry matter basis (w/w) ||||||
| Ingredient | Example 13 | Example 14 | Example 15 | Example 16 | Example 17 | Example 18 |
|---|---|---|---|---|---|---|
| Poultry and fish products | 15 | 30 | 49 | 58 | 22 | 2.8 |
| Cereal grains | 20 | 11.8 | 25 | 10 | 24 | 3.1 |
| Fat | 2.6 | 6.8 | 5.5 | 2.9 | 6 | 2.5 |
| Humectants | 15 | 20 | 5 | 2 | 12 | 2 |
| Vitamins | 0.1 | 0.05 | 0 | 0.05 | 0.1 | 0.05 |
| Minerals | 0.1 | 0.05 | 0 | 0.05 | 0.1 | 0.05 |
| Fiber | 4.4 | 3 | 5 | 2 | 5 | 7 |
| Rosemary extract | 0.00 | 0.5 | 2.5 | 5.0 | 25.0 | 75.0 |
| Rosemarinic acid | 0.0 | 0.0 | 0.0 | 0.0 | 0.0 | 2.5 |
| Coffee extract | 0.0 | 0.0 | 2.5 | 0.0 | 0.0 | 0.0 |
| Coffeic acid | 0.0 | 0.0 | 0.5 | 0.0 | 0.0 | 0.0 |
| Turmeric extract | 0.0 | 0.0 | 0.0 | 0.0 | 2.5 | 0.0 |
| Cucurmin | 0.0 | 0.0 | 0.0 | 0.0 | 0.5 | 0.0 |
| Blueberry extract | 25.0 | 0.0 | 0.0 | 0.0 | 0.0 | 0.0 |
| Grapeseed extract | 0.0 | 0.0 | 0.0 | 5.0 | 0.0 | 0.0 |
| Tea extract | 0.0 | 25.0 | 0.0 | 0.0 | 0.0 | 0.0 |
| Lutein | 15.0 | 0.0 | 5.0 | 15.0 | 0.0 | 5.0 |
| Lysine | 2.5 | 2.5 | 0.0 | 0.0 | 2.5 | 0.0 |
| Taurine | 0.3 | 0.3 | 0.0 | 0.0 | 0.3 | 0.0 |

The moist compositions of Examples 13, 14, 15, 16, 17 and 18 can be made by milling and mixing the cereal grains with vitamins and minerals and fiber sources and lutein, lysine, rosemary extract or rosemarinic acid or coffee extract or coffeic acid or turmeric extract or cucurmin or blueberry extract or grapeseed extract or tea extract, and taurine. Then, add the cereal grains to the meat products and other protein sources with humectants to control water activity and mold. Extrude the ingredients into desired shape. Package the finished product.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for promoting eye health in an animal consisting essentially of administering therapeutically effective amounts of a composition consisting essentially of a tea extract selected from the group consisting of black tea, oolong tea, green tea and combinations thereof, lutein, lysine, and CoQ10.

2. The method of claim 1, wherein the composition is administered orally.

3. The method of claim 2, wherein the composition is an edible composition.

4. The method of claim 3, wherein the tea extract is 0.01% to 90% of the edible composition by weight of the composition.

5. The method of claim 4, wherein the tea extract is 3% to 10% of the edible composition by weight of the composition.

6. The method of claim 3, wherein the lutein is 0.01% to 20% of the edible composition by weight of the composition.

7. The method of claim 6, wherein the lutein is 0.05% to 10% of the edible composition by weight of the composition.

8. The method of claim 3, wherein the lysine is 0.05% to 10% of the edible composition by weight of the composition.

9. The method of claim 8, wherein the lysine is 1.5% to 5% of the edible composition by weight of the composition.

10. The method of claim 3, wherein the CoQ10 is 0.01% to 10% of the edible composition by weight of the composition.

11. The method of claim 10, wherein the CoQ10 is 0.2% to 5% of the edible composition by weight of the composition.

12. The method of claim 3, wherein the edible composition is complete and nutritionally balanced.

13. The method of claim 1, wherein the administration is parenteral, intravenous, or subcutaneous.

14. The method of claim 1, wherein the animal is a companion animal.

15. The method of claim 14, wherein the animal is a dog, cat, or ferret.

16. The method of claim 15, wherein the animal is a puppy.

17. The method of claim 15, wherein the animal is a kitten.

18. The method of claim 15, wherein the animal is a senior animal.

19. The method of claim 15, wherein the animal is an adult animal.

* * * * *